United States Patent [19]

Rody et al.

[11] 4,177,186

[45] Dec. 4, 1979

[54] STABILIZATION OF LIGHT-SENSITIVE POLYMERS

[75] Inventors: Jean Rody, Basel, Switzerland; Gerd Greber, Bad Vöslau, Austria; Helmut Müller, Binningen, Switzerland

[73] Assignee: Ciba-Geigy Corporation, Ardsley, N.Y.

[21] Appl. No.: 853,655

[22] Filed: Nov. 21, 1977

Related U.S. Application Data

[63] Continuation-in-part of Ser. No. 687,825, May 19, 1976, abandoned.

[30] Foreign Application Priority Data

May 28, 1975 [CH] Switzerland ................... 6831/75

[51] Int. Cl.$^2$ ...................... C07D 211/18; C08K 5/34
[52] U.S. Cl. .......................... 260/45.8 N; 546/14; 106/169; 106/163 R
[58] Field of Search ............ 260/45.8 N, 293.63, 260/293.64, 293.65, 293.69, 293.51; 546/14, 45.8 N

[56] References Cited

U.S. PATENT DOCUMENTS

| | | | |
|---|---|---|---|
| 3,513,170 | 5/1970 | Murayama et al. | 260/45.8 N |
| 3,840,494 | 10/1974 | Murayama et al. | 260/45.8 N |

FOREIGN PATENT DOCUMENTS

| | | | |
|---|---|---|---|
| 1326889 | 8/1973 | United Kingdom | 260/293.63 |
| 406833 | 6/1974 | U.S.S.R. | 260/293.63 |

OTHER PUBLICATIONS

Shapiro et al., Polymer Science USSR, vol. A14, (1973), pp. 3034-3043.

*Primary Examiner*—H. S. Cockeram
*Attorney, Agent, or Firm*—Vincent J. Cavalleri

[57] ABSTRACT

4-Siloxy-derivatives of sterically hindered piperidines are good light-stabilizers for organic polymers, especially for polyolefins. The stabilizers are added in an amount of from 0.01 to 5% by weight, preferably 0.02 to 1% by weight based on the polymer. The new compounds are obtainable by O-silylation of the corresponding 4-hydroxypiperidines.

13 Claims, No Drawings

STABILIZATION OF LIGHT-SENSITIVE POLYMERS

This application is a continuation-in-part application of co-pending application Ser. No. 687,825, filed May 19, 1976, now abandoned.

This invention relates to novel 4-siloxy derivatives of alkylated piperidines useful for stabilizing organic polymers against photo-deterioration, and a composition of matter stabilized against photo-deterioration comprising an organic polymer, normally subject to deterioration by light, and a 4-siloxy derivative of an alkylated piperidine.

A. B. Shapiro et al. in Polymer Science USSR, Vol. A 15 (1973), page 3034 have disclosed-inter alia-radicalic derivatives of 4-siloxypiperidine-1-oxyls of formula

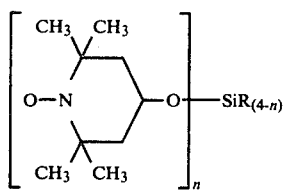

wherein n is 1, 2 or 3 and R is alkyl or phenyl. These compounds are stabilizers against the thermal and photochemical deterioration of polypropylene. These radicalic compounds are of deep red colour and their addition to plastics accordingly causes a discoloration of the substrates. Therefore these compounds could not get technical importance up to now.

In the German laid open patent application No. 2.204.659 there are disclosed compounds of the formula

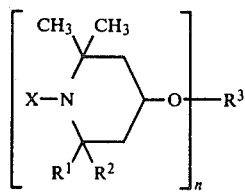

and their use as stabilizers for polymers. Within this general formula inter alia orthosilicates are included; where $R^3$ is a silicon atom and n is 4.

Now is has been found that 4-silyloxy derivatives of 2,2,6,6-tetraalkylated piperidines show an excellent stabilizing action on light-sensitive-polymers and show certain advantages over the known orthosilicates as for example an enhanced compatibility with certain polymeric substrates.

The compounds of this invention, usable as stabilizers, are defined by formula I

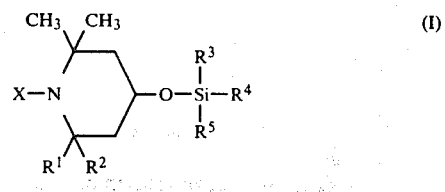

wherein
$R^1$ and $R^2$ independently from one another represent alkyl having 1-4 C-atoms or together with the C-atom to which they are attached form a cyclopentane or cyclohexane or a 2,2,6,6-tetramethyl-piperidine ring, $R^3$ is hydrogen, methyl, phenyl or vinyl, $R^4$ and $R^5$ independently from one another represent hydrogen, methyl, phenyl, vinyl, alkoxy having 1-8 C-atoms, alkoxy-alkoxy having 3-10 C-atom, cyclohexyloxy, aralkoxy having 7 or 8 C-atoms, phenoxy which is unsubstituted or substituted by chlorine, alkyl or alkoxy having each 1-4 C-atoms, or a group of the formula Ia

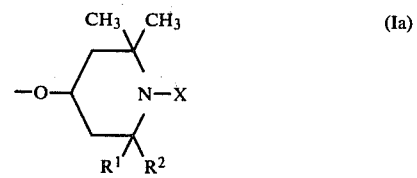

and, if $R^3$ and $R^4$ are hydrogen, methyl, phenyl or vinyl, $R^5$ may also be a group of the formula Ib

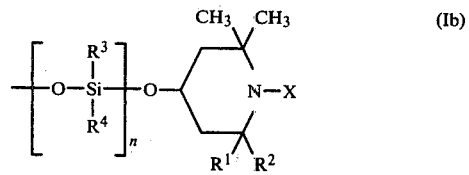

wherein n is an integer of from 1 to 20, and
X is hydrogen, alkyl having 1-12 C-atoms, alkenyl having 3-6 C-atoms, alkoxyalkyl having 3-14 C-atoms, aralkyl having 7 or 8 C-atoms or an aliphatic acyl group having 1-4 C-atoms or one of the groups $-CH_2COOR^6$, $-CH_2-CH(R^7)-OR^8$ or $-COOR^9$ wherein $R^6$ is alkyl having 1-8 C-atoms, alkenyl having 3-6 C-atoms, phenyl, aralkyl having 7 or 8 C-atoms or cyclohexyl, $R^7$ is hydrogen, methyl or phenyl, $R^8$ is hydrogen or an aliphatic, aromatic, araliphatic or alicyclic acyl group having up to 18 C-atoms, which may be substituted in its aryl moiety with chlorine, alkyl having 1-4 C-atoms, alkoxy having 1-8 C-atoms and/or hydroxy, and $R^9$ is alkyl having 1-8 C-atoms, benzyl, phenyl or cyclohexyl with the proviso that, when X is hydrogen and $R^3$ is phenyl, one of $R^4$ and $R^5$ is different from a 2,2,6,6-tetramethylpiperidine-4-oxy residue.

As far as these piperidine derivatives are basic they form salts with acids and these salts are usable as stabilizers in the same way as the bases.

When $R^1$ or $R^2$ is an alkyl group having 1-4 C-atoms it may be a methyl, ethyl, propyl, isopropyl, n-butyl or isobutyl group.

When $R^4$ or $R^5$ is an alkoxy group having 1-8 C-atoms it may be e.g. a methoxy, ethoxy, isopropoxy, butoxy, hexoxy or octoxy group. $R^4$ or $R^5$ as alkoxyalkoxy having 3-10 C-atoms may be e.g. a methoxyethoxy, ethoxypropoxy, propoxybutoxy, butoxyethoxy, hexoxyethoxy or tert.butoxyethoxy group, preferably it may be an alkoxyethoxy group.

When $R^4$ is an aralkoxy group having 7 or 8 C-atoms, it may be a benzoxy or phenethoxy group.

When $R^4$ or $R^5$ is a substituted phenoxy group it may be substituted with chlorine, alkyl having 1–4 C-atoms or alkoxy having 1–4 C-atoms and $R^4$ or $R^5$ may be e.g. a chlorophenoxy, toluyloxy, xylyloxy, 4-tert.butylphenoxy, 3-ethoxyphenoxy or 4-methoxyphenoxy group.

When X is an alkyl group having from 1 to 12 C-atoms it may be e.g., methyl, ethyl, n-propyl, n-butyl, n-hexyl, n-octyl, n-decyl or n-dodecyl.

When X is an alkenyl group having from 3 to 6 C-atoms it may be e.g., allyl, 2-butenyl or 2-hexenyl; especially an alkenyl group having 3 or 4 C-atoms, most especially allyl.

When X is an alkoxyalkyl group having from 3 to 14 C-atoms, it may be e.g. 2-methoxyethyl, 2-ethoxyethyl, 2-n-butoxyethyl, 3-n-butoxypropyl, 2-octoxyethyl or 2-dodecyloxyethyl, especially an alkoxyethyl group.

When X is an aralkyl group having 7 or 8 carbon atoms it may be e.g., benzyl or phenylethyl, preferably it is benzyl.

When X is an aliphatic acyl group having 1–4 C-atoms, it may be e.g. a formyl, acetyl, propionyl, butyryl, acryloyl or crotonyl group.

When X is a group of the formula $-CH_2-COOR^6$ or $-COOR^9$, $R^6$ and $R^9$ may be an alkyl group having from 1 to 8 carbon atoms, e.g., methyl, ethyl, isopropyl, n-butyl, isobutyl, tert.butyl, isopentyl or octyl; an alkenyl group having 3 to 6 carbon atoms, e.g., allyl, 2-butenyl or 2-hexenyl; a phenyl group; an aralkyl group having 7 or 8 carbon atoms, e.g., benzyl or phenylethyl; or a cyclohexyl group; especially an alkyl group from 1 to 4 carbon atoms.

When X is a group of the formula $-CH_2CH(R^7)-OR^8$, $R^7$ may be a hydrogen atom, a methyl group or phenyl group, preferably hydrogen, and $R^8$ may be a hydrogen atom or an aliphatic, aromatic, araliphatic or alicyclic acyl group having up to 18 carbon atoms, for example $R^8$ may be an acetyl, propionyl, butyryl, octanoyl, dodecanoyl, stearoyl, acryloyl, benzoyl, 4-chlorobenzoyl, toluoyl, 4-isopropylbenzoyl, 2,4-dichlorobenzoyl, 4-methoxybenzoyl, 3-butoxybenzoyl, 2-hydroxybenzoyl, 3,5-di-tert.butyl-4-hydroxybenzoyl, $\beta$(3,5-di-tert.butyl-4-hydroxyphenyl)propionyl, phenylacetyl, cinnamoyl, hexahydrobenzoyl, 1- or 2-naphthoyl or decahydronaphthoyl group.

Acid-addition salts of compounds of formula I may be salts from inorganic acids such as sulfuric, hydrochloric or phosphoric acid; from organic carboxylic acids such as formic, acetic, valeric, stearic, oxalic, adipic, sebacic, maleic, benzoic, p-tert.butyl-benzoic, 3,5-ditert.-butyl-4-hydroxybenzoic, salicyclic or terephthalic acid; from sulfonic acids such as methanesulfonic or p-toluenesulfonic acid; or from organic phosphorus acids such as diphenyl phosphoric acid or phenyl phosphonic acid.

Preferred are compounds of formula I wherein $R^1$ and $R^2$ are each methyl, $R^3$ is hydrogen, methyl, phenyl or vinyl, $R^4$ and $R^5$ are independently of another hydrogen, methyl, phenyl, vinyl, alkoxy having 1–8 C-atoms, phenoxy which is unsubstituted or substituted by an alkyl group having 1–4 C-atoms, or a residue of formula Ia, and, if $R^3$ and $R^4$ are hydrogen, methyl, phenyl or vinyl, $R^5$ may also be a residue of formula Ib, and X is hydrogen, alkyl having 1–4 C-atoms, benzyl or an aliphatic acyl group having 1–4 C-atoms, with the proviso that, when X is hydrogen and $R^3$ is phenyl, one of $R^4$ and $R^5$ is different from a 2,2,6,6-tetramethylpiperidine-4-oxy residue. This proviso also applies to the further preferred embodiments listed below.

Particularly preferred are compounds of formula I wherein $R^1$ and $R^2$ are each methyl, X is hydrogen, alkyl having 1–4 carbon atoms or acetyl, $R^3$ is hydrogen, methyl or phenyl and $R^4$ and $R^5$ are methyl, phenyl or a residue of formula Ia in which residue of formula Ia $R^1$ and $R^2$ are each methyl and X is hydrogen, alkyl having 1–4 C-atoms or acetyl, and especially compounds of formula I wherein $R^1$ and $R^2$ are each methyl, X is hydrogen or methyl, $R^3$ and $R^4$ are methyl or phenyl and $R^5$ is methyl, phenyl or a residue of formula Ia in which residue of formula Ia $R^1$ and $R^2$ are each methyl and X is hydrogen or methyl.

Most preferred are compounds of formula I wherein $R^1$ and $R^2$ are each methyl, X is hydrogen or methyl, $R^3$ is methyl and $R^4$ and $R^5$ are methyl, phenyl or a residue of formula Ia in which residue of formula Ia $R^1$ and $R^2$ are each methyl and X is hydrogen or methyl.

The following is a list of specific 4-siloxypiperidines of formula I. It is, however, to be understood that the present invention is not limited to the use of these illustrating compounds.

2,2,6,6-tetramethyl-4-trimethylsiloxypiperidine
1,2,2,6,6-pentamethyl-4-trimethylsiloxypiperidine
2,2,6,6-tetramethyl-4-triphenylsiloxypiperidine
1,2,2,6,6-pentamethyl-4-triphenylsiloxypiperidine
1-acetyl-2,2,6,6-tetramethyl-4-triphenylsiloxypiperidine
1-acrylol-2,2,6,6-tetramethyl-4-triphenylsiloxypiperidine
1-crotonyl-2,2,6,6-tetramethyl-4-trimethylsiloxypiperidine
1-$\beta$-hydroxyethyl-2,2,6,6-tetramethyl-4-triphenylsiloxypiperidine
1-$\beta$-benzoyloxyethyl-2,2,6,6-tetramethyl-4-trimethylsiloxypiperidine
1-$\beta$-acetyloxyethyl-2,2,6,6-tetramethyl-4-trimethylsiloxypiperidine
1-ethoxycarbonylmethyl-2,2,6,6-tetramethyl-4-tribenzylsiloxypiperidine
1-ethoxycarbonyl-2,2,6,6-tetramethyl-4-triphenylsiloxypiperidine
dimethyl-bis-(2,2,6,6-tetramethylpiperidin-4-oxy)-silane
dimethyl-bis-(1,2,2,6,6-pentamethylpiperidin-4-oxy)-silane
diphenyl-bis-(2,2,6,6-tetramethylpiperidin-4-oxy)-silane
diphenyl-bis-(1,2,2,6,6-pentamethylpiperidin-4-oxy)-silane
diphenyl-bis-(1-allyl-2,2,6,6-tetramethylpiperidin-4-oxy)-silane
diphenyl-bis-(1-acetyl-2,2,6,6-tetramethylpiperidin-4-oxy)-silane
diphenyl-bis-(1-butyl-2,2,6,6-tetramethylpiperidine-4-oxy)-silane
diphenyl-bis-(1-benzyl-2,2,6,6-tetramethylpiperidin-4-oxy)-silane
methyl-phenyl-bis-(2,2,6,6-tetramethylpiperidin-4-oxy)-silane
methyl-phenyl-bis-(1,2,2,6,6-pentamethylpiperidin-4-oxy)-silane
methyl-bis-(2,2,6,6-tetramethylpiperidin-4-oxy)-silane
methyl-bis-(1,2,2,6,6-pentamethylpiperidin-4-oxy)-silane
methyl-bis-(1-acetyl-2,2,6,6-tetramethylpiperidin-4-oxy)-silane
phenyl-bis-(2,2,6,6-tetramethylpiperidin-4-oxy)-silane phenyl-bis-(1,2,2,6,6-pentamethylpiperidin-4-oxy)-silane
tri-(2,2,6,6-tetramethylpiperidin-4-oxy)-silane
tri-(1,2,2,6,6-pentamethylpiperidin-4-oxy)-silane
tri-(1-allyl-2,2,6,6-tetramethylpiperidin-4-oxy)-silane
methyl-tris-(2,2,6,6-tetramethylpiperidin-4-oxy)-silane
methyl-tris-(1,2,2,6,6-pentamethylpiperidine-4-oxy)-silane
methyl-tris-(1-allyl-2,2,6,6-tetramethylpiperidin-4-oxy)-silane
methyl-tris-(1-benzyl-2,2,6,6-tetramethylpiperidin-4-oxy)-silane
methyl-tris-(1-acetyl-2,2,6,6-tetramethylpiperidin-4-oxy)-silane
phenyl-tris-(1,2,2,6,6-pentamethylpiperidin-4-oxy)-silane
phenyl-tris-(1-acetyl-2,2,6,6-tetramethylpiperidin-4-oxy)-silane
2,2,6,6-tetramethyl-4-(phenyl-dimethylsiloxy)-piperidine
1,2,2,6,6-pentamethyl-4-(phenyl-dimethylsiloxy)-piperidine
1,3-bis-(2,2,6,6-tetramethylpiperidine-4-oxy)-1,1,3,3-tetramethyl-disiloxane
1,3-bis-(1,2,2,6,6-pentamethylpiperidine-4-oxy)-1,1,3,3-tetramethyl-disiloxane The 4-siloxypiperidines of formula I can be prepared by silylation of the corresponding 4-hydroxypiperidines II

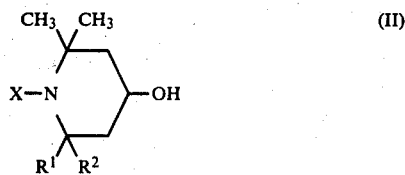

with silane derivatives of the formulae Y—Si($R^3$)($R^4$)($R^5$), (Y)$_2$Si($R^3$)($R^4$) or (Y)$_3$SiR$^3$ wherein Y represents a substituent known to be reactive in O-silylation for example it may be halogen, alkoxy, dialkylamino or acyloxy. Preferably silane derivatives are used in this silylation reaction, wherein Y is chlorine, which are known as chlorosilanes.

Examples for those chlorosilanes are methyltrichlorosilane, dimethyldichlorosilanes, phenylmethyldichlorosilane, diphenyldichlorosilane, methyldichlorosilane, phenyltrichlorosilane, phenoxydimethylchlorosilane or 1,1,3,3-tetramethyl-1,3-dichlorodisiloxane, or mixtures of $\omega,\omega'$-dichloro-polysiloxanes.

The silylation with chlorosilanes is usually carried out in inert solvents, e.g. in hydrocarbons or ethers, such as benzene, toluene, cyclohexane, diethylether or tetrahydrofuran. Stoichiometric amounts of tertiary amines are usually added for neutralizing the formed hydrogen chloride, e.g. triethyl amine, tributyl amine or dimethyl aniline. The tertiary amine can also be used in large excess when it is used as solvent. This latter method is of advantage, when a 4-hydroxypiperidine of formula II is silylated, wherein X is hydrogen, and a N-silylation should be avoided.

In accordance with the invention, it has now been discovered that the 4-siloxypiperidines of formula I can effectively stabilize a wide range of organic polymers against light-induced deterioration with superior compatibility with polymer substrates. Polymers which can be stabilized in this way include:

1. Polymers which are derived from mono- or diolefines, for example polyethylene which can optionally be crosslinked, polypropylene, polyisobutylene, polymethylbutene-1, polymethylpentene-1, polyisoprene, polybutadiene.
2. Mixtures of the homopolymers cited under (1), for example mixtures of polypropylene and polyethylene, polypropylene and polybutene-1, polypropylene and polyisobutylene.
3. Copolymers of the monomers based on the homopolymers cited under (1), for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene.
4. Polystyrene.
5. Copolymers of styrene and of α-methylstyrene with dienes or acrylic derivatives, for example styrene/butadiene copolymers, styrene/acrylonitrile copolymers, styrene/acrylonitrile/methylacrylate copolymers, styrene/acrylonitrile copolymers modified with acrylic ester polymers to provide impact strength as well as styrene polymers modified with EPDM to provide impact strength and blockcopolymers of styrene.
6. Graft copolymers of styrene, for example the graft polymer of styrene to polybutadiene, the graft polymer of styrene with acrylonitrile to polybutadiene as well as mixtures thereof with the copolymers cited under (5), commonly referred to as acrylonitrile/butadiene/styrene or ABS plastics.
7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.
8. Polymers which are derived from α,β-unsaturated acids and derivatives thereof, polyacrylates and polymethacrylates, polyacrylic amides and polyacrylonitrile.
9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.
10. Homopolymers and copolymers which are derived from epoxides, for example polyethylene oxide, polypropylene-oxide, or their copolymers with bis-glycidyl ethers.
11. Polyacetals, for example polyoxymethylene, as well as polyoxymethylenes which contain ethylene oxide as comonomer.
12. Polyphenylene oxides.
13. Polyurethanes and polyureas.
14. Polycarbonates.
15. Polysulphones.
16. Polyamides and copolyamides which are derived from diamines and dicarboxylic acids and/or from aminocarboxylic acids or the corresponding lactames, for example polyamide 6, polyamide 6/6, polyamide 6/10, polyamide 11, polyamide 12.
17. Polyesters which are derived from dicarboxylic acids and dialcohols and/or from hydroxycarboxylic 18. Cross-linked polymers which are derived from aldehydes on the one hand and from phenols, ureas and melamines on the other, for example phenol/formaldehyde, urea/formaldehyde and melamine/formaldehyde resins.
19. Alkyd resins, for example glycerol/phthalic acid resins and mixtures thereof with melamine/formaldehyde resins.
20. Unsaturated polyester resins which are derived from copolyesters of saturated and unsaturated dicarboxylic acids with polyhydric alcohols as well as from vinyl compounds as corss-linking agents and also the halogen-containing, flame-resistant modifications thereof.
21. Cross-linked epoxide resins, derived from polyepoxides, e.g. from bis-glycidyl-ethers or from cycloaliphatic diepoxides.
22. Natural polymers, for example cellulose, rubber, proteins as well as the chemically modified homologous derivatives thereof, for example cellulose acetates, cellulose propionates and cellulose butyrates and the cellulose ethers, for example methyl cellulose.
23. Silicone-resins, silicone-rubbers and silicone oils.

From these the polymers of group 1–6, 13 and 16 are of particular interest as the application of the stabilizers according to the invention has an outstanding effect on these polymers.

The compounds of formula I are added to the substrates in an amount of from 0.01 to 5% by weight, based on the weight of the polymer.

Preferably the stabilizers are incorporated in an amount of from 0.02 to 1.0%, especially 0.05 to 0.5% by weight based on the polymer. The incorporation is achieved by mixing at least one of the compounds of formula I and optionally other additives with the polymer according to the methods known in plastics technology. The mixing may be achieved before or during the shaping prozessing, or by coating the polymer with the dissolved or dispersed stabilizer, followed by evaporation of the solvent.

The stabilized polymer compositions of the invention may optionally also contain various conventional additives, such as the following:

1. Antioxidants 1.1 Simple 2,6-dialkylphenols, such as, for example, 2,6-di-tert.butyl-4-methylphenol, 2-tert.butyl-4,6-dimethylphenol, 2,6-di-tert.butyl-4-methoxymethylphenol and 2,6-dioctadecyl-4-methylphenol.

1.2 Derivatives of alkylated hydroquinones, such as, for example, 2,5-di-tert.butyl-hydroquinone, 2,5-di-tert.amylhydroquinone, 2,6-di-tert.butyl-hydroquinone, 2,5-di-tert.butyl-4-hydroxy-anisole, 3,5-di-tert.butyl-4-hydroxy-anisole, tris-(3,5-di-tert.butyl-4-hydroxyphenyl) phosphite, 3,5-di-tert.butyl-4-hydroxyphenyl stearate and bis-(3,5-di-tert.butyl-4-hydroxyphenyl) adipate.

1.3 Hydroxylated thiodiphenyl ethers, such as, for example, 2,2'-thio-bis-(6-tert.butyl-4-methylphenol), 2,2'-thio-bis-(4-octylphenol), 4,4'-thio-bis-(6-tert.butyl-3-methylphenol), 4,4'-thio-bis-(3,6-di-sec.amylphenol), 4,4'-thio-bis-(6-tert.butyl-2-methylphenol) and 4,4'-bis-(2,6-dimethyl-4-hydroxyphenyl) disulphide.

1.4 Alkylidene-bisphenols, such as, for example, 2,2'-methylene-bis-(6-tert.butyl-4-methylphenol), 2,2'-methylene-bis-(6-tert.butyl-4-ethylphenol), 4,4'-methylene-bis-(6-tert.butyl-2-methylphenol), 4,4'-methylene-bis-(2,6-di-tert.butylphenol), 2,6-di-(3-tert.butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)butane, 1,1-bis-(5-tert.butyl-4-hydroxy-2-methylphenyl)-butane, 2,2-bis-(5-tert.butyl-4-hydroxy-2-methylphenyl)-butane, 2,2-bis-(3,5-di-tert.butyl-4-hydroxyphenyl)-propane, 1,1,3-tris-(5-tert.butyl-4-hydroxy-2-methylphenyl)-butane, 2,2-bis-(5-tert.butyl-4-hydroxy-2-methylphenyl)-4-n-dodecylmercapto-butane, 1,1,5,5-tetra-(5-tert.butyl-4-hydroxy-2-methylphenyl)-pentane and ethylene glycol bis-[3,3-bis-(3'-tert.butyl-4'-hydroxyphenyl)-butyrate].

1.5 O—, N— and S—benzyl compounds, such as, for example, 3,5,3',5'-tetra-tert.butyl-4,4'-dihydroxydibenzyl ether, 4-hydroxy-3,5-dimethylbenzyl-mercaptoacetic acid octadecyl ester, tri-(3,5-di-tert.butyl-4-hydroxybenzyl)-amine and bis-(4-tert.butyl-3-hydroxy-2,6-dimethylbenzyl)dithiol terephthalate.

1.6 Hydroxybenzylated malonic esters, such as, for example, 2,2-bis-(3,5-di-tert.butyl-2-hydroxybenzyl)-malonic acid dioctadecyl ester, 2-(3-tert.butyl-4-hydroxy-5-methylbenzyl)-malonic acid dioctadecyl ester, 2,2-bis-(3,5-di-tert.butyl-4-hydroxybenzyl)-malonic acid didodecylmercaptoethyl ester and 2,2-bis-(3,5-di-tert.butyl-4-hydroxybenzl)-malonic acid di-[4-(1,1,3,3-tetramethylbutyl)-phenyl] ester.

1.7 Hydroxybenzyl-aromatics, such as, for example, 1,3,5-tri-(3,5-di-tert.butyl-4-hydroxybenzyl)-2,4,6-trimethylbenzene, 1,4-di-(3,5-di-tert.butyl-4-hydroxybenzyl)-2,3,5,6-tetramethylbenzene and 2,4,6-tri-(3,5-di-tert.butyl-4-hydroxybenzyl)-phenol.

1.8 s-Triazine compounds, such as, for example, 2,4-bis-octylmercapto-6-(3,5-di-tert.butyl-4-hydroxyanilino)-s-triazine, 2-octylmercapto-4,6-bis-(3,5-di-tert.butyl-4-hydroxy-anilino)-s-triazine, 2-octylmercapto-4,6-bis-(3,5-di-tert.butyl-4-hydroxy-phenoxy)-s-triazine, 2,4,6-tris-(3,5-di-tert.butyl-4-hydroxyphenoxy)-s-triazine, 2,4,6-tris-(3,5-di-tert.butyl-4-hydroxyphenylethyl)-s-triazine and 1,3,5-tris-(3,5-di-tert.butyl-4-hydroxybenzyl)-isocyanurate.

1.9 Amides of β-(3,5-di-tert.butyl-4-hydroxyphenyl)-propionic acid, such as, for example, 1,3,5-tris-(3,5-di-tert.-butyl-4-hydroxyphenyl-propionyl)-hexahydro-s-triazine and N,N'-di-(3,5-di-tert.butyl-4-hydroxyphenyl-propionyl)-hexamethylenediamine.

1.10 Esters of β-(3,5-di-tert.butyl-4-hydroxyphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, tris-hydroxyethylisocyanurate and 4-hydroxymethyl-1-phospha-2,6,7-trioxabicyclo[2,2,2]octane.

1.11 Esters of β-(5-tert.butyl-4-hydroxy-3-methylphenyl)-propionic acid with monohydric or polyhydric alcohols such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, trishydroxyethylisocyanurate and 4-hydroxymethyl-1-phospha-2,6,7-trioxabicyclo[2,2,2]octane.

1.12 Esters of 3,5-di-tert.butyl-4-hydroxyphenylacetic acid with monohydric or polyhydric alcohols such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, tris-hydroxyethylisocyanurate and 4-hydroxymethyl-1-phospha-2,6,7-trioxabicyclo[2,2,2]-octane.

1.13 Acylaminophenols, such as, for example, N-(3,5-di-tert.butyl-4-hydroxyphenyl)-stearic acid amide and N,N'-di-(3,5-di-tert.butyl-4-hydroxyphenyl)-thio-bis-acetamide.

1.14 Benzylphosphonates, such as, for example, 3,5-di-tert.butyl-4-hydroxybenzyl-phosphonic acid dimethyl ester, 3,5-di-tert.butyl-4-hydroxybenzyl-phosphonic acid diethyl ester, 3,5-di-tert.-butyl-4-hydroxybenzyl-phosphonic acid dioctadecyl ester and 5-tert.butyl-4-hydroxy-3-methylbenzyl-phosphonic acid dioctadecyl ester.

1.15 Aminoaryl derivatives, such as, for example, phenyl-1-naphthylamine, phenyl-2-naphthylamine, N,N'-diphenyl-p-phenylenediamine, N,N'-di-1-naphthyl-p-phenylenediamine, N,N'-di-2-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2-dihydroquinoline, monooctyliminodibenzyl and dioctyliminodibenzyl, and polymerised 2,2,4-trimethyl-1,2-dihydroquinoline.

2. UV absorbers and light stabilisers 2.1. 2-(2'-Hydroxyphenyl)-benztriazoles, such as, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.-butyl-, 3'-α-methylbenzyl-5'-methyl-, 3'-α-methylbenzyl-5'-methyl-5-chloro-, 4'-hydroxy-, 4'-methoxy-, 4'-octoxy-, 3', 5'-di-tert.amyl-, 3'-methyl-5'-carbomethoxyethyl- and 5-chloro-3',5'-di-tert.-amyl-derivative.

2.2 2,4-Bis-(2'-hydroxyphenyl)-6-alkyl-s-triazines, such as, for example, the 6-ethyl-, 6-heptadecyl-, or 6-undecyl-derivative.

2.3 2-Hydroxy-benzophenones, such as, for example, the 4-hydroxy-, 4-methoxy-, 4-octoxy-, 4-decyloxy, 4-dodecyloxy-, 4-benzyloxy-, 4,2',4'-trihydroxy- or 2'-hydroxy-4,4'-dimethoxy-derivative.

2.4 1,3-Bis-(2'-hydroxybenzoyl)-benzenes, such as, for example, 1,3-bis-(2'-hydroxy-4'-hexyloxy-benzoyl)-benzene, 1,3-bis-(2'-hydroxy-4'-octyloxy-benzoyl)-benzene and 1,3-bis(2'-hydroxy-4'-dodecyloxy-benzoyl)-benzene.

2.5 Esters of optionally substituted benzoic acids, such as, for example, phenyl salicylate, octylphenyl salicylate, dibenzoylresorcinol, bis-(4-tert.-butylbenzoyl)-resorcinol, benzoylresorcinol and 3,5-di-tert.-butyl-4-hydroxybenzoic acid 2,4-di-tert.butyl-phenyl ester or octadecyl ester or 2-methyl-4,6-di-tert.butyl-phenyl ester.

2.6. Acrylates, such as, for example, α-cyano-β,β-diphenylacrylic acid ethyl ester or isooctyl ester, α-carbomethoxycinnamic acid methyl ester, α-cyano-β-methyl-p-methoxy-cinnamic acid methyl ester or butyl ester and N-(β-carbomethoxy-vinyl)-2-methyl-indoline.

2.7. Oxalic acid diamides, such as, for example, 4,4'-di-octyloxy-oxanilide, 2,2'-di-octyloxy-5,5'-di-tert.butyloxanilide, 2,2'-di-dodecyloxy-5,5'-di-tert.butyl-oxanilide, 2-ethoxy-2'-ethyl-oxanilide, N,N'-bis-(3-dimethylaminopropyl)-oxalamide, 2-ethoxy-5-tert.butyl-2'-ethyl-oxanilide and its mixture with 2-ethoxy-2'-ethyl-5,4-di-tert.butyl-oxanilide and mixtures of ortho- and para-methoxy- as well as of o- and p-ethoxy-disubstituted oxanilides.

3. Phosphites, such as, for example, triphenyl phosphite, diphenylalkyl phosphites, phenyldialkyl phosphites, tri-(nonylphenyl) phosphite, trilauryl phosphite, trioctadecyl phosphite, 3,9-di-isodecyloxy-2,4,8,10-tetraoxa-3,9-diphosphaspiro[5,5]-undecane and tri-(4-hydroxy-3,5-di-tert.butylphenyl) phosphite.

4. Compounds which destroy peroxide, such as, for example, esters of β-thiodipropionic acid, for example the lauryl, stearyl, myristyl or tridecyl esters, salts of 2-mercaptobenzimidazole, for example the Zn salt, and diphenylthiourea.

5. Basic co-stabilisers, such as, for example, melamine, benzoguanamine, polyvinylpyrrolidone, dicyandiamide, triallylcyanurate, urea derivatives, hydrazine derivatives, amines, polyamides, polyurethanes, and alkali metal salts and alkaline earth metal salts of higher fatty acids, for example Ca stearate, Zn stearate, Mg stearate, Na ricinoleate or K palmitate.

6. Nucleating agents, such as, for example, 4-tert.butyl-benzoic acid, adipic acid and diphenylacetic acid.

7. Other additives, such as, for example, plasticisers, lubricants, emulsifiers, fillers, carbon black, asbestos, kaolin, talc, glass fibres, pigments, flameproofing agents and antistatic agents.

The use of the stabilizers of formula I with the above-listed antioxidants is particularly effective for the stabilization of olefin polymers.

Synergistic effects may appear in using such known additives in combination with the stabilizers of formula I. This is especially true with the additives listed as group 2 and 3.

The invention is further illustrated by the following Examples in which all parts and percentages are by weight.

EXAMPLES 1-9

38 g (0.15 moles) of diphenyldichlorosilane are dropped within 15 minutes with stirring to a solution of 50 g (0.3 moles) of 2,2,6,6-tetramethyl-4-hydroxypiperidine in 500 g dry triethylamine at a temperature of 85° C. During the reaction triethylamine hydrochloride is precipitating. After a further hour of heating to 90° C. the cooled reaction mixture is filtered by suction. The filtered off hydrochloride after drying weighs 41 g according a nearly quantitative conversion. The filtrate is distilled fractionally yielding 66 g diphenyl-bis(2,2,6,6-tetramethylpiperidin-4-oxy)-silane (Compound Nr. 1) boiling at 185° C./0.001 Torr. The oily distillate crystallizes on staying, the crystals melt at 69°–71° C. The yield is 90%.

Analysis ($C_{30}H_{46}N_2O_2Si$): Calculated: C, 72.82; H, 9.36; N, 5.66; Si, 5.67%. Found: C, 72.7; H, 9.6; N, 5.5; Si, 6.0%.

Following the same procedure starting from 2,2,6,6-tetramethyl-4-hydroxypiperidine and the corresponding stoichiometric amounts of (a) trimethylchlorosilane
(b) phenyltrichlorosilane
(c) methyltrichlorosilane
(d) dimethyldichlorosilane
(e) methyl-phenyldichlorosilane
(f) methyldichlorosilane
(g) trichlorosilane
(h) triphenylchlorosilane there are prepared the following compounds of formula I:

(a) 2,2,6,6-tetramethyl-4-trimethylsiloxy-piperidine (Compound No. 2), b.p. 85°–87° C./12 torr, yield 94%.

Analysis ($C_{12}H_{27}NOSi$): Calculated: C, 62.81; H, 11.86; N, 6.11; Si, 12.24%.
Found: C, 63.1; H, 11.8; N, 6.0; Si, 12.4.

(b) phenyl-tris(2,2,6,6-tetramethylpiperidin-4-oxy)-silane (Compound No. 3), b.p. 192°–195° C./0.001 torr, yield 85%.

Analysis ($C_{33}H_{59}N_3O_3Si$): Calculated: C, 69.06; H, 10.36; N, 7.32; Si, 4.89%. Found: C, 68.7; H, 10.5; N, 7.4; Si, 5.2.

(c) methyl-tris(2,2,6,6-tetramethylpiperidin-4-oxy)-silane (Compound No. 4), b.p. 155°–160° C./0.001 torr, yield 70%.

Analysis ($C_{28}H_{57}N_3O_3Si$): Calculated: C, 65.70; H, 11.22; N, 8.21; Si, 5.49%. Found: C, 65.3; H, 11.3; N, 8.2; Si, 5.9.

(d) dimethyl-bis(2,2,6,6-tetramethylpiperidin-4-oxy)-silane (Compound No. 5), b.p. 110°–115° C./0.001 torr, yield 70%.

Analysis ($C_{20}H_{42}N_2O_2Si$): Calculated: C, 64.81; H, 11.42; N, 7.56; Si, 7.58%. Found: C, 64.6; H, 11.5; N, 7.2; Si, 7.3.

(e) methyl-phenyl-bis(2,2,6,6-tetramethylpiperidin-4-oxy)-silane (Compound No. 6), b.p. 160°–165° C./0.001 torr, yield 80%.

Analysis ($C_{25}H_{44}N_2O_2Si$): Calculated: C, 69.38; H, 10.24; N, 6.47; Si, 6.49%. Found: C, 68.9; H, 10.1; N, 6.0; Si, 7.3.

(f) methyl-bis(2,2,6,6-tetramethylpiperidin-4-oxy)-silane (Compound No. 7), b.p. 115°–120° C./0.001 torr., m.p. 35°–37° C., yield 53%.

Analysis ($C_{19}H_{40}N_2O_2Si$): Calculated: C, 63.98; H, 11.30; N, 7.85; Si, 7.87%. Found: C, 64.1; H, 11.5; N, 7.9; Si, 7.8%.

(g) tris(2,2,6,6-tetramethylpiperidin-4-oxy)-silane (Compound No. 8), b.p. 170° C./0.001 torr, yield 47%.

Analysis ($C_{27}H_{55}N_3O_3Si$): Calculated: C, 65.14; H, 11.14; N, 8.44; Si, 5.64%. Found: C, 65.1; H, 11.1; N, 8.5; Si, 6.1%.

(h) 2,2,6,6-tetramethyl-4-triphenylsiloxy-piperidine (Compound No. 9) m.p. 109°.

EXAMPLE 10 AND 11

To a solution of 17.1 g (0.1 mole) of 1,2,2,6,6-pentamethyl-4-hydroxy-piperidine and 10.1 g (0.1 mole) of triethylamine in 200 ml tetrahydrofuran are dropped 10.9 g (0.1 mole) of trimethylchlorosilane under stirring and heating to reflux temperature. The reaction is completed after a further hour of refluxing. The precipitated triethylamine hydrochloride is filtered off by suction and washed at the funnel with tetrahydrofuran.

The filtrate is evaporated and the only residue distilled under reduced pressure. There is obtained 21.7 g of 1,2,2,6,6-pentamethyl-4-trimethylsiloxy-piperidine (Compound No. 10) distilling at 100°–101° C. at 12 torr (yield 90%). Instead of the tetrahydrofuran also benzene, dioxane or xylene can be used as solvent without reducing the yields. When 29.4 g of triphenylchlorosilane are used instead of the trimethylchlorosilane in the above procedure, there are obtained 29.4 g (90.5%) of 1,2,2,6,6-pentamethyl-4-triphenylsiloxy-piperidine (Compound No. 11), melting at 109°–110° C.

EXAMPLE 12

34.2 g (0.2 mole) of 1,2,2,6,6,-pentamethyl-4-hydroxypiperidine dissolved in 250 ml benzene are reacted with 20.3 g (0.1 mole) of 1,3-dichloro-1,1,3,3-tetramethyldisiloxane in the presence of 20.2 g (0.2 mole) of trimethylamine at room temperature. The reaction mixture is stirred for further 2 hours at reflux temperature. After cooling the precipitated hydrochloride is filtered off and the filtrate is evaporated. The viscous residue is triturated with hexane and the filtered hexane solution is evaporated to dryness. There remain 40 g (80%) of 1,3-bis-(1,2,2,6,6-pentamethylpiperidin-4-oxy)-1,1,3,3-tetramethyldisiloxane (Compound No. 12).

Analysis ($C_{24}H_{52}O_3N_2Si_2$): Calculated: C, 60.96; H, 11.09; N, 5.93; Si, 11.88%. Found: C, 60.3; H, 11.5; N, 5.7; Si, 12.4.

EXAMPLE 13

100 parts polypropylene powder (Moplen, fibre grade, Montedison Comp.) and 0.2 parts octadecyl β-(3,5-di-tert.butyl-4-hydroxyphenyl)-propionate as antioxidant and 0.25 or 0.5 parts of a light-stabiliser listed in Table 1 are homogenised in a Brabender plastograph during 10 minutes at 200° C. The resulting mass is pressed to a 2 to 3 mm thick sheet in a laboratory press. The sheet is hot pressed in a hydraulic press during 6 minutes at 260° C. and a pressure of 12 tons yielding a 0.5 mm thick film which is quenched immediately in cold water. By the same procedure a 0.1 mm film is made from the 0.5 mm film.

Test specimens of 66×44 mm are cut from the film and irradiated in a "Xenotest 150" radiation equipment. The content of carbonyl groups of the irradiated films is periodically controlled by infrared spectroscopy. The increase of carbonyl groups characterised by the infrared extinction at 5.85μ is a relevant measure for the light-induced deterioration of polypropylene (see L. Balaban et al., J. Polymer Sci., Part C, 22 (1969), 1059–1071) and is, according to experience, accompanied by a gradual loss of the mechanical properties of the polymer. Thus the film is completely brittle when the carbonyl extinction becomes 0.30. The protective action of the different light-stabilisers of the invention is shown in Table 1.

Table 1

| Compound (No. given in Examples 1–11) | Irradiation time (hours) | CO extinction (5.85 μ) |
|---|---|---|
| none | 1050 | 0.30 |
| No. 1  0.25% | 8000 | 0.05 |
| 5  0.25% | 5200 | 0.03 |
| 10  0.5% | 23'000 | 0.3 |
| 11  0.5% | 8000 | <0.01 |

What we claim is:
1. A compound of formula I

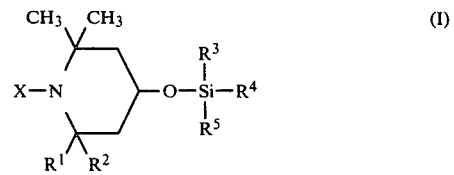

wherein

R¹ and R² independently from one another represent alkyl having 1–4 C-atoms or together with the C-atom to which they are attached form a cyclopentane or cyclohexane or a 2,2,6,6-tetramethylpiperidine ring, R³ is hydrogen, methyl, phenyl or vinyl, R⁴ and R⁵ independently from one another represent hydrogen, methyl, phenyl, vinyl, alkoxy having 1–8 C-atoms, alkoxyalkoxy having 3–10 C-atom, cyclohexyloxy, aralkoxy having 7 or 8 C-atoms, phenoxy which is unsubstituted or substituted by chlorine, alkyl or alkoxy having each 1–4 C-atoms, or a group of the formula Ia

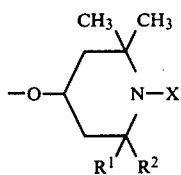

and, if R³ and R⁴ are hydrogen, methyl, phenyl or vinyl, R⁵ may also be a group of the formula Ib

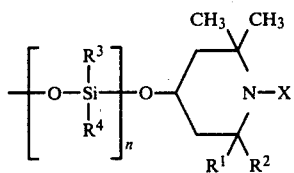

wherein n is an integer of from 1 to 20, and

X is hydrogen, alkyl having 1–12 C-atoms, alkenyl having 3–6 C-atoms, alkoxyalkyl having 3–14 C-atoms, aralkyl having 7 or 8 C-atoms or an aliphatic acyl group having 1–4 C-atoms or one of the groups —CH₂COOR⁶, —CH₂—CH(R⁷)—OR⁸ or —COOR⁹ wherein R⁶ is alkyl having 1–8 C-atoms, alkenyl having 3–6 C-atoms, phenyl, aralkyl having 7 or 8 C-atoms or cyclohexyl, R⁷ is hydrogen, methyl or phenyl, R⁸ is hydrogen or an aliphatic, aromatic, araliphatic or alicyclic acyl group having up to 18 C-atoms, which may be substituted in its aryl moiety with chlorine, alkyl having 1–4 C-atoms, alkoxy having 1–8 atoms and/or hydroxy, and R⁹ is alkyl having 1–8 C-atoms, benzyl, phenyl or cyclohexyl, with the proviso that, when X is hydrogen and R³ is phenyl, one of R⁴ and R⁵ is different from a 2,2,6,6-tetramethylpiperidine-4-oxy residue.

2. A compound as claimed in claim 1 wherein
R¹ and R² are each methyl,
R³ is hydrogen, methyl, phenyl or vinyl,
R⁴ and R⁵ are independently of another hydrogen, methyl, phenyl, vinyl, alkoxy having 1–8 C-atoms, phenoxy which is unsubstituted or substituted by an alkyl group having 1–4 C-atoms, or a residue of formula Ia, and, if R³ and R⁴ are hydrogen, methyl, phenyl or vinyl.
R⁵ may also be a residue of formula Ib, and
X is hydrogen, alkyl having 1 to 4 C-atoms, benzyl or an aliphatic acyl group having 1–4 C-atoms.

3. A compound as claimed in claim 1 wherein R¹ and R² are each methyl, X is hydrogen, alkyl having 1–4 C-atoms or acetyl, R³ is hydrogen, methyl or phenyl and R⁴ and R⁵ are methyl, phenyl or a residue of formula Ia in which residue of formula Ia R¹ and R² are each methyl and X is hydrogen, alkyl having 1–4 C-atoms or acetyl.

4. A compound as claimed in claim 1 wherein R¹ and R² are each methyl, X is hydrogen or methyl, R³ and R⁴ are methyl or phenyl and R⁵ is methyl, phenyl or a residue of formula Ia in which residue of formula Ia R¹ and R² are each methyl and X is hydrogen or methyl.

5. A compound as claimed in claim 1 wherein R¹ and R² are each methyl, X is hydrogen or methyl, R³ is methyl and R⁴ and R⁵ are methyl, phenyl or a residue of formula Ia in which residue of formula Ia R¹ and R² are each methyl and X is hydrogen or methyl.

6. The compound of claim 1, 2,2,6,6-tetramethyl-4-triphenylsilyloxypiperidine.

7. The compound of claim 1, 1,2,2,6,6-pentamethyl-4-triphenylsilyloxypiperidine.

8. The compound of claim 1, diphenyl-bis(2,2,6,6-tetramethylpiperidine-4-oxy)silane.

9. The compound of claim 1, diphenyl-bis(1,2,2,6,6-pentamethylpiperidine-4-oxy)silane.

10. The compound of claim 1, dimethyl-bis(2,2,6,6-tetramethylpiperidine-4-oxy)silane.

11. A composition of matter stabilized against photodeterioration comprising an organic polymer, normally subject to deterioration by light, and from 0.01 to 5.0 percent by weight of a compound as claimed in claim 1.

12. A composition as claimed in claim 11, wherein the organic polymer is a polyolefin or a styrene homo- or copolymer.

13. A composition as claimed in claim 11, wherein the organic polymer is a polyurethane or a polyamide.

* * * * *